United States Patent [19]

Shyu

[11] Patent Number: 4,708,337
[45] Date of Patent: Nov. 24, 1987

[54] AUTOMATIC TREADMILL

[75] Inventor: Jia-Ming Shyu, Taipei, Taiwan

[73] Assignee: Industrial Technology Research Institute, Hsin-Chu Sheng, Taiwan

[21] Appl. No.: 813,655

[22] Filed: Dec. 26, 1985

[51] Int. Cl.$^4$ ............................................. A63B 23/06
[52] U.S. Cl. ...................................................... 272/69
[58] Field of Search ........................... 272/69; 340/541

[56] References Cited

U.S. PATENT DOCUMENTS

| | | | |
|---|---|---|---|
| 3,643,943 | 2/1972 | Erwin, Jr. et al. | 272/69 |
| 3,675,640 | 7/1972 | Gatts | 272/69 |
| 4,209,776 | 6/1980 | Frederick | 340/541 |
| 4,278,095 | 7/1981 | Lapeyre | 272/69 |
| 4,364,556 | 12/1982 | Otte | 272/69 |

Primary Examiner—Leo P. Picard
Attorney, Agent, or Firm—Cushman, Darby & Cushman

[57] ABSTRACT

An improved treadmill comprises at track mechanism wherein the rotational speed of the tread belt is automatically controlled to suit the physical condition of the user, and a slope adjusting mechanism is associated with the track mechanism to enable the track mechanism to operate at a slope. The treadmill further comprises a controller having a microprocessor formed therein for inputting control data, processing and recording operation status data, and outputting/displaying those stored data. There are ports of sensors to collect various exercise data such as speed, distance, slope, pulse rate, duration, etc. The controller then enables the treadmill to operate in accordance with a predetermined sequence of functions and to adapt to the condition of the user, while at the same time the controller stores/displays exercise data, such as the pulse rate, pace, number of steps taken, heat dissipated, etc.

9 Claims, 29 Drawing Figures

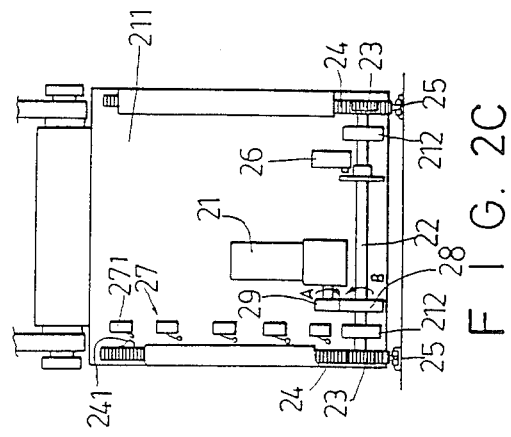
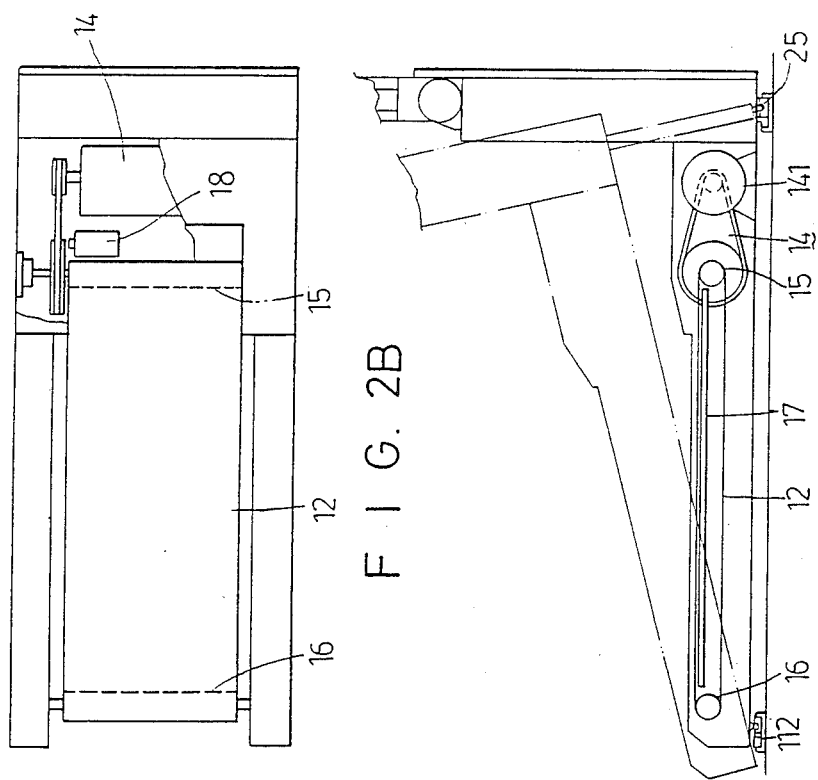

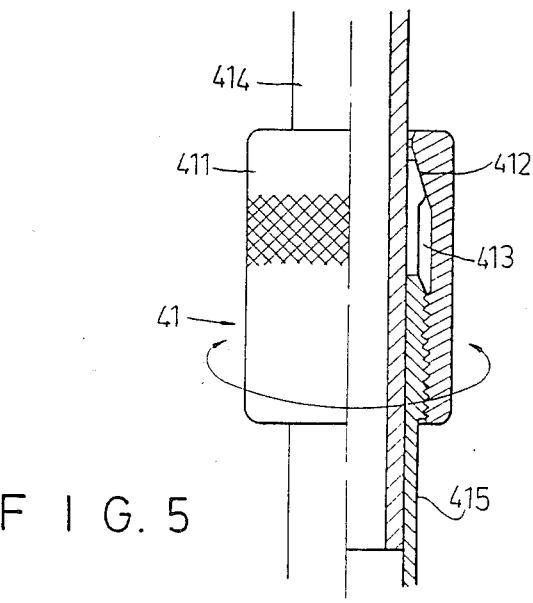
F I G. 5
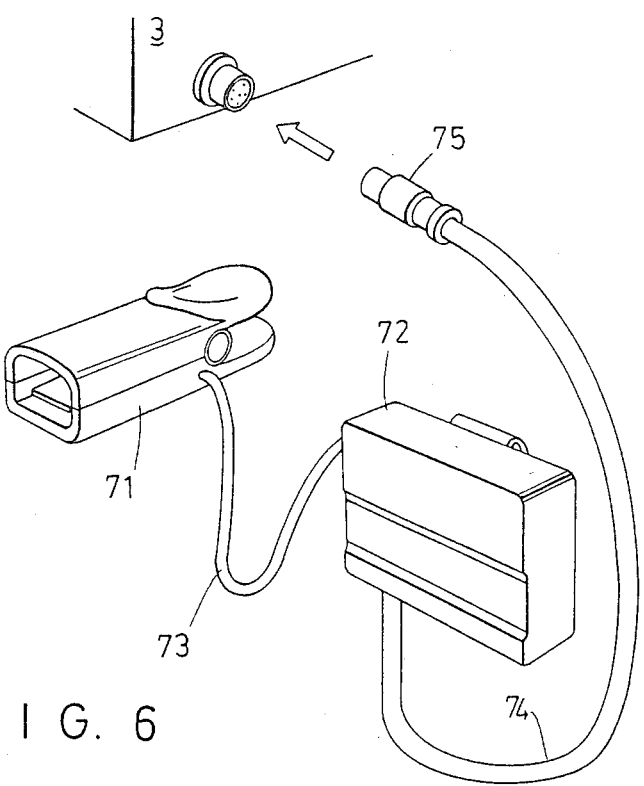
F I G. 6

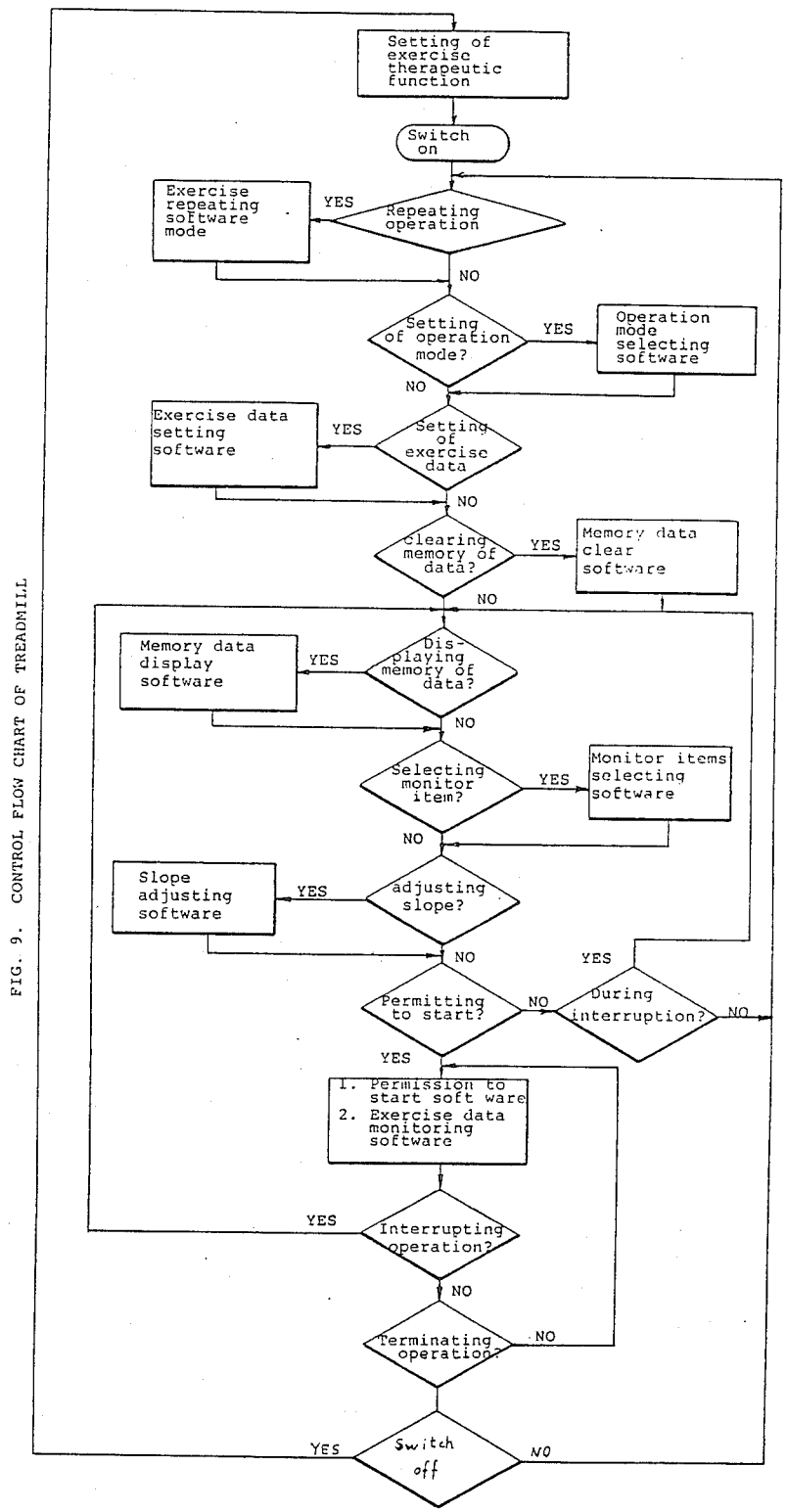
FIG. 9. CONTROL FLOW CHART OF TREADMILL

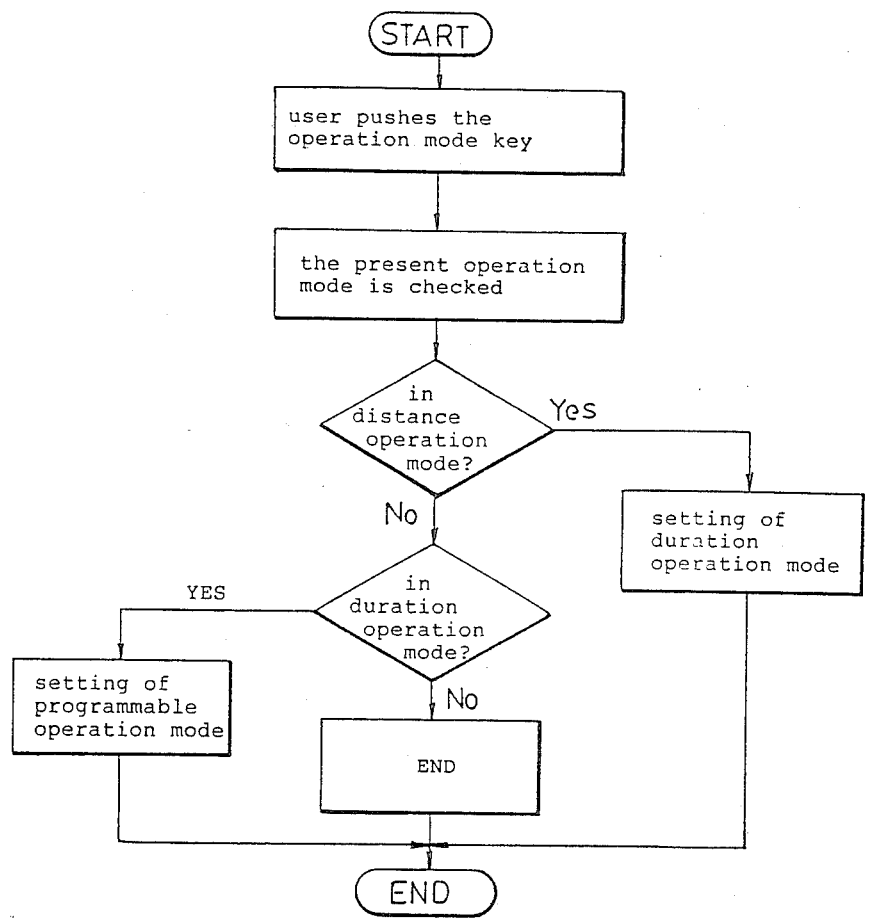
FIG. 10 Flow Chart for Setting of Operation Mode
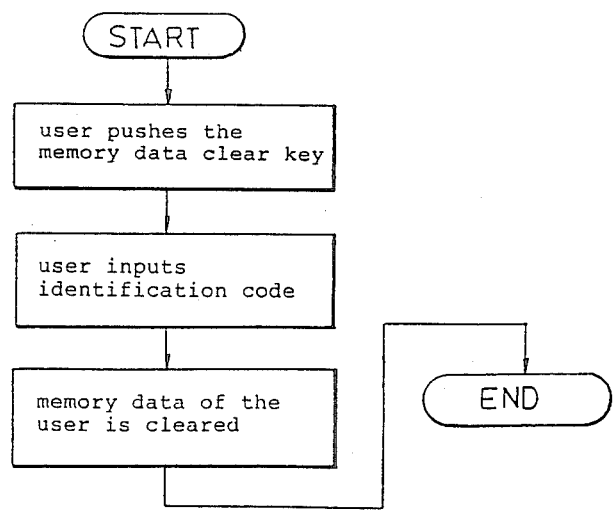
FIG. 11. Flow Chart for Clearing Memory Data FIG. 12. FLOW CHART FOR REPEATING OPERATION
FIG. 13. FLOW CHART FOR EXERCISE DATA SETTING
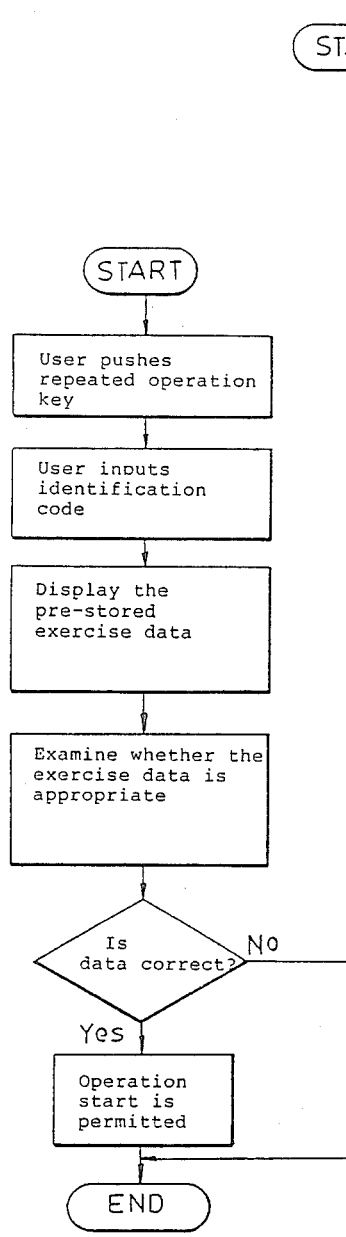
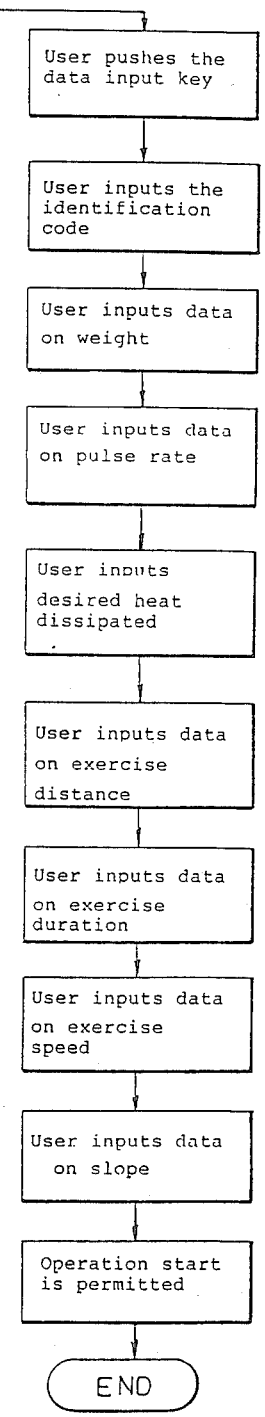

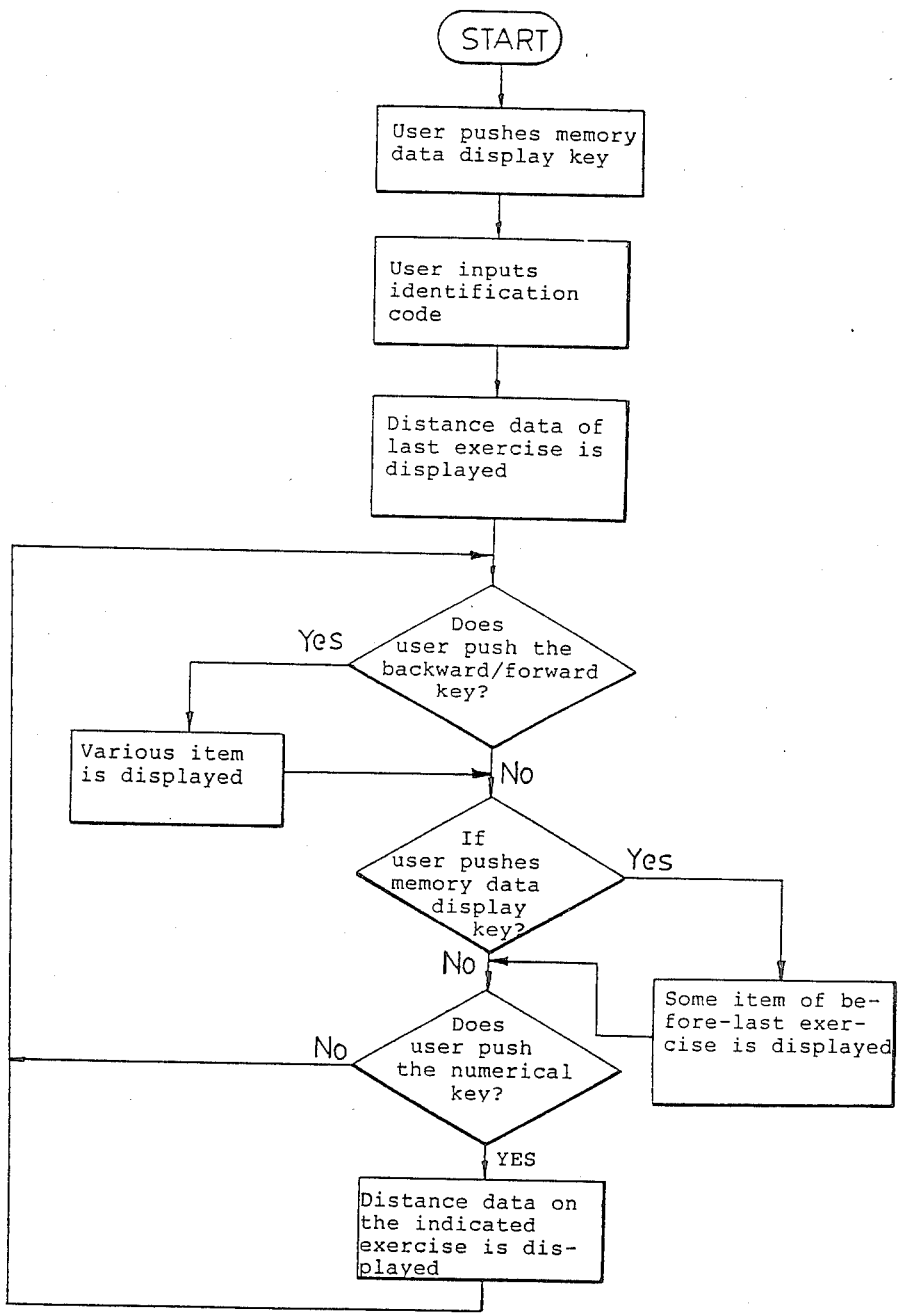
FIG. 14. FLOW CHART FOR DISPLAY MEMORY DATA

FIG. 15-1 FLOW CHART FOR EXERCISE DISTANCE MONITOR
FIG. 15-2 FLOW CHART FOR EXERCISE DURATION MONITOR
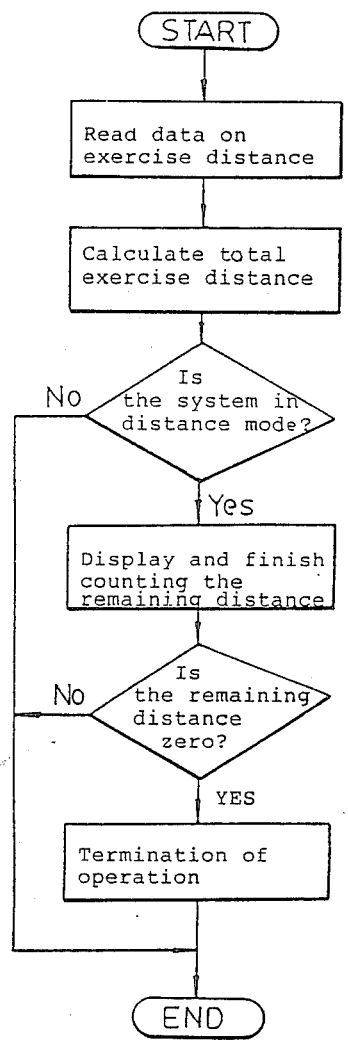
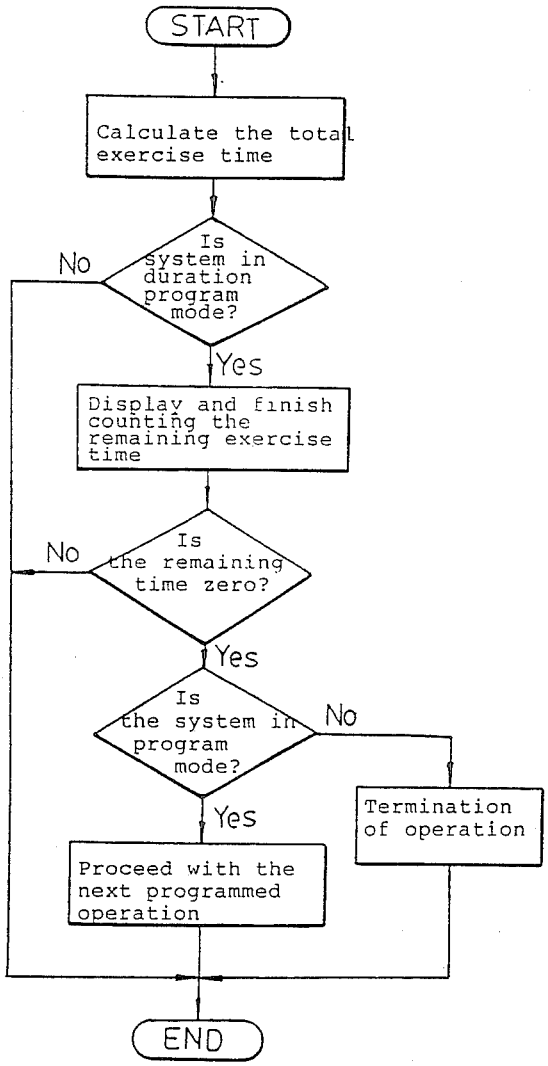
Remark: The exercise duration monitoring will be executed once per second FIG. 15-3
FLOW CHART FOR MONITOR
OF NUMBER OF STEPS
FIG. 15-4
FLOW CHART FOR
PACE MONITOR
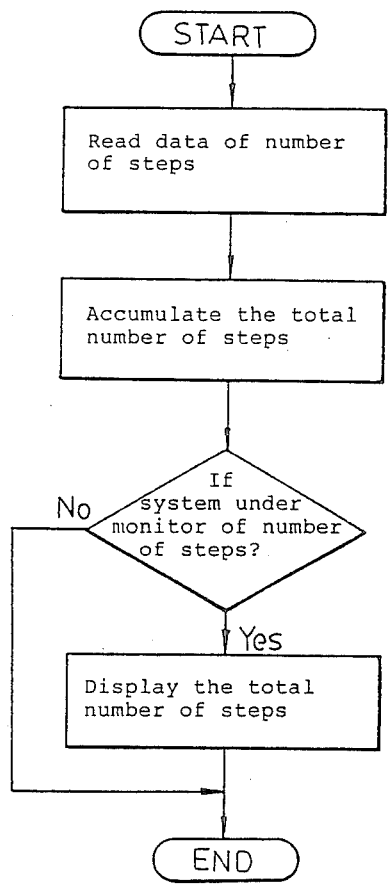
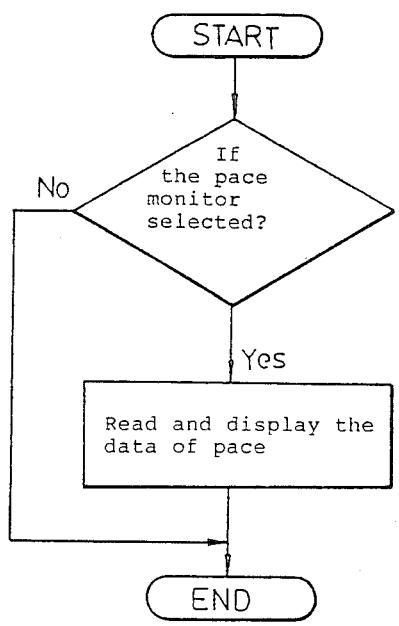

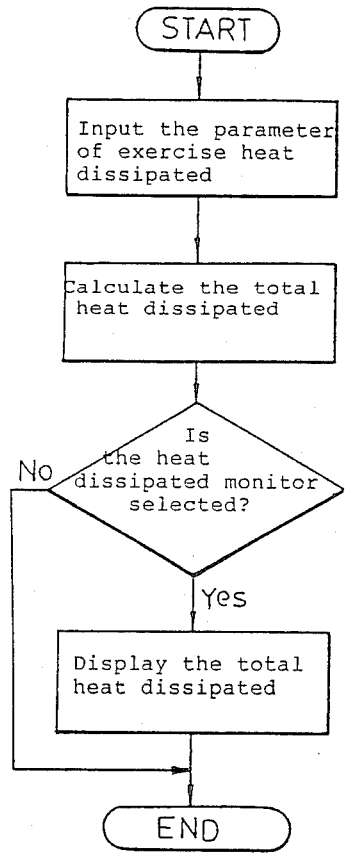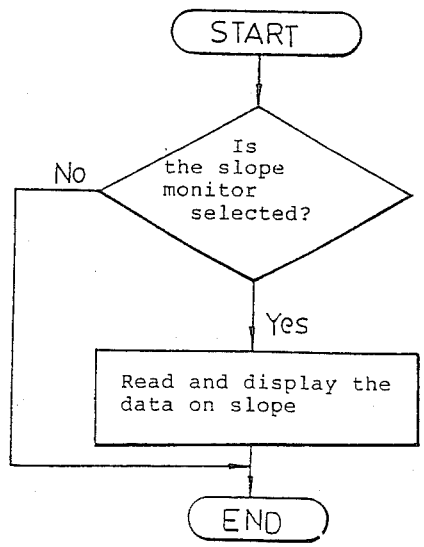
FIG. 15-5. FLOW CHART FOR MONITOR OF HEAT DISSIPATED
FIG. 15-6. FLOW CHART FOR MONITOR OF SLOPE

FLOW CHART FOR EXERCISE SPEED MONITOR

FLOW CHART FOR PULSE RATE MONITOR

FLOW CHART FOR
INTERRUPTION OF OPERATION

FLOW CHART FOR
TERMINATION OF OPERATION

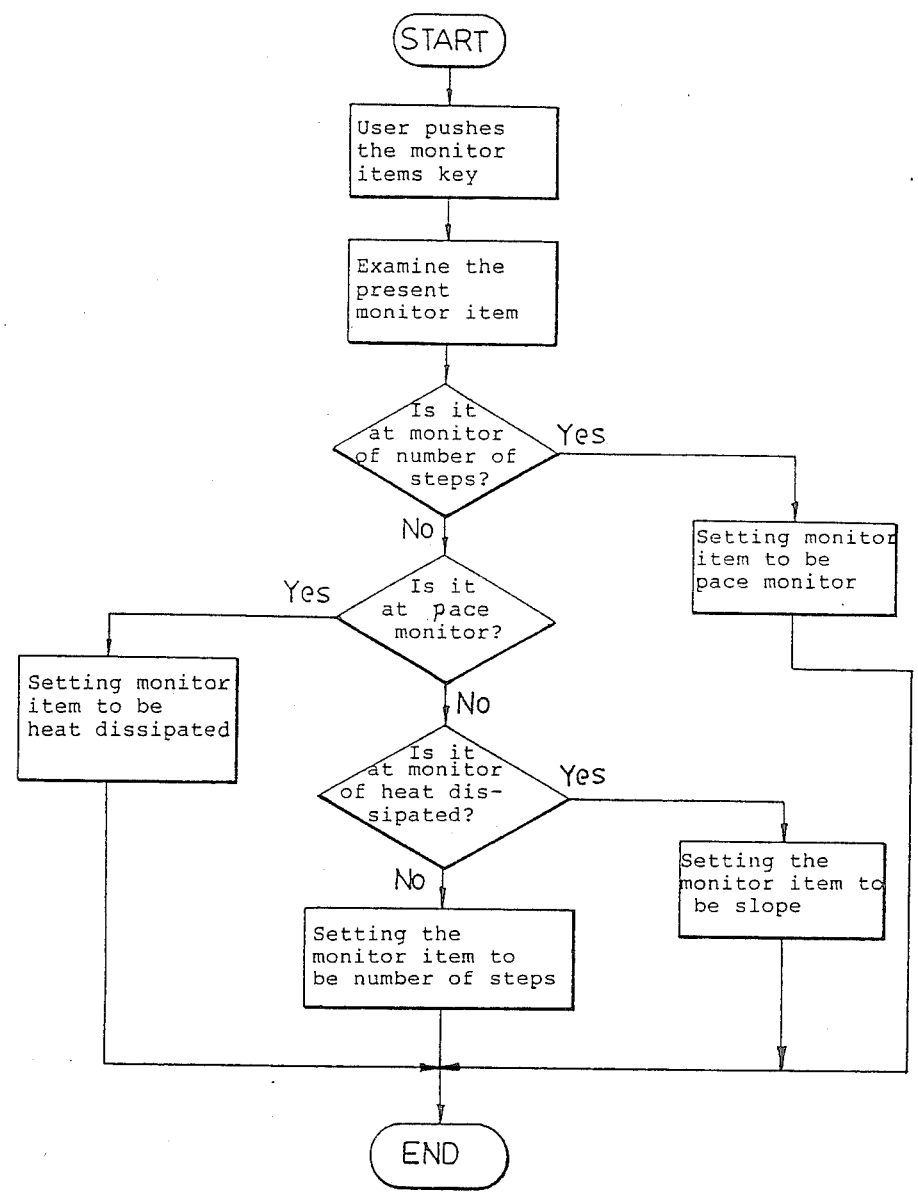
FIG. 18 FLOW CHART FOR SELECTING MONITOR ITEM

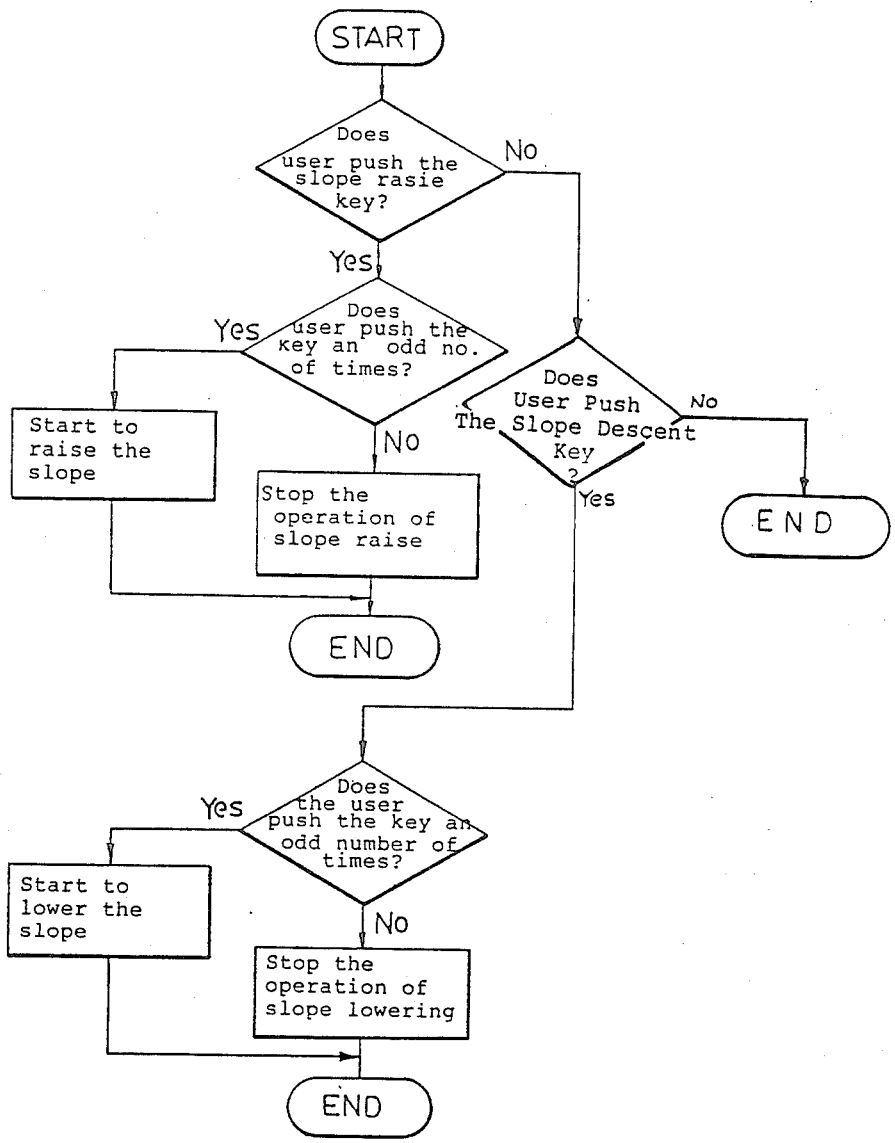
FIG. 19 FLOW CHART FOR SLOPE ADJUSTMENT

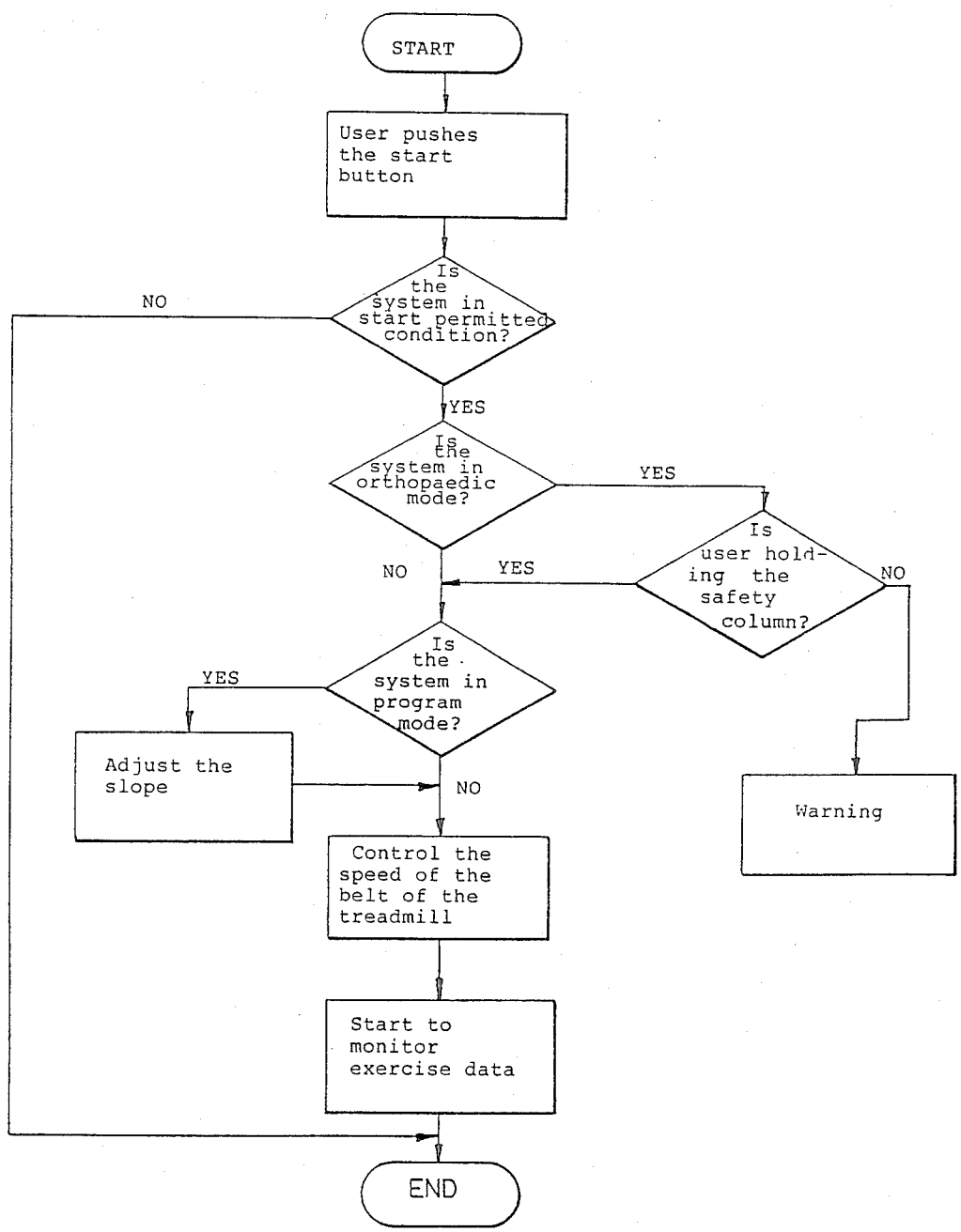
FIG. 20 FLOW CHART FOR START OPERATION

AUTOMATIC TREADMILL

BACKGROUND OF THE INVENTION

The present invention relates to a treadmill, particularly to one capable of automatically choosing different operation modes and displaying the physical condition of the user during its use.

We know proper physical exercise may improve metabolism and enhances blood circulation. People need physical exercise to remain healthy. However, in our modern daily life, most people do not have much time for outdoor physical exercise. Also, many people can or will not perform serious physical exercise outdoors because of factors such as their occupation, personality or physical obstacles such as having had a stroke.

Recently, treadmills for people to walk or run on have become increasingly popular. The principal advantage of a treadmill is that it is handy for indoor physical exercise. However, conventional treadmills have several disadvantages. The most commonly used treadmill has only a rotatable tread belt for the user to stand upon and walk or run on. Because the speed of rotation of the tread belt is not adjustable, users do not have the same feeling as running outdoors. In addition, the flat tread belt is not like real ground which usually has bumps and slopes. Furthermore, conventional treadmills do not have any means for recording the physical state of the user or a display to let the user know his own physical condition so that he will not overexert himself.

SUMMARY OF THE INVENTION

The main object of the present invention is to provide an improved treadmill, especially an automatic one, which contains various features that conventional treadmills do not have.

Another object of the present invention is to provide a treadmill which can be used for ordinary running exercise and also for the purpose of orthopedic training.

An important feature of the present invention is a supersonic detecting apparatus to sense and determine the position of the user and to generate an output signal to automatically control the rotating speed of the tread belt for the safety of the user.

Another feature of the treadmill according to the present invention is the adoption of a microprocessor for controlling the period of operation, angle and change of slope of the pave belt and also for displaying aspects of the physical condition of the user, such as his pulse rate.

A further feature of the treadmill according to the present invention is to provide a controller for receiving reference data of the user such as his age, weight, an identification code, etc. By using the controller, the user can set the operation mode of the treadmill and also have recorded and displayed all his exercise data.

To these objects, the treadmill of the present invention comprises a track means having a rotation driving means to rotate a tread belt on the track means and a slope adjusting means to adjust the slope of the track means, a controller connected to the track means for input of reference data and generation of control signals for operation mode, speed and slope adjustment, and a microprocessor having stored therein a predetermined program for processing data input to the controller, generating output data and storing useful physical condition data concerning the user.

BRIEF DESCRIPTION OF THE DRAWINGS

These and other objects, advantages and features of the treadmill according to the present invention will become apparent from the following detailed description of a preferred embodiment with reference to the accompanying drawings, wherein:

FIGS. 2A, 2B and 2C are illustrative front, top and right side views of the treadmill according to the present invention, showing the slope adjusting mechanism for the track;

FIG. 5 is a partial sectional view of the height adjusting means of the handrails;

FIG. 6 is a perspective view of a linked set of a pulse rate detector and a detector of the number of steps taken;

FIG. 9 is a flow chart of the program for the overall control system of the treadmill;

FIG. 10 is a flow chart for the program of setting of the operation mode;

FIG. 11 is a flow chart for clearing the memory data program;

FIG. 12 is a flow chart for the program of repeating the operation;

FIG. 13 is a flow chart for the exercise data setting program;

FIG. 14 is a flow chart for the displaying memory data program;

FIGS. 15-1 to 15-8 are flow charts for the programs of monitors for exercise distance, exercise duration, number of steps, pace, heat dissipated, slope, speed, and pulse rate respectively;

FIG. 18 is a flow chart for the program of selecting monitor items;

FIG. 19 is a flow chart for the slope adjustment program; and

FIG. 20 is a flow chart for the starting operation program.

DETAILED DESCRIPTION OF THE PREFERRED EMBODIMENT

Figure 1:
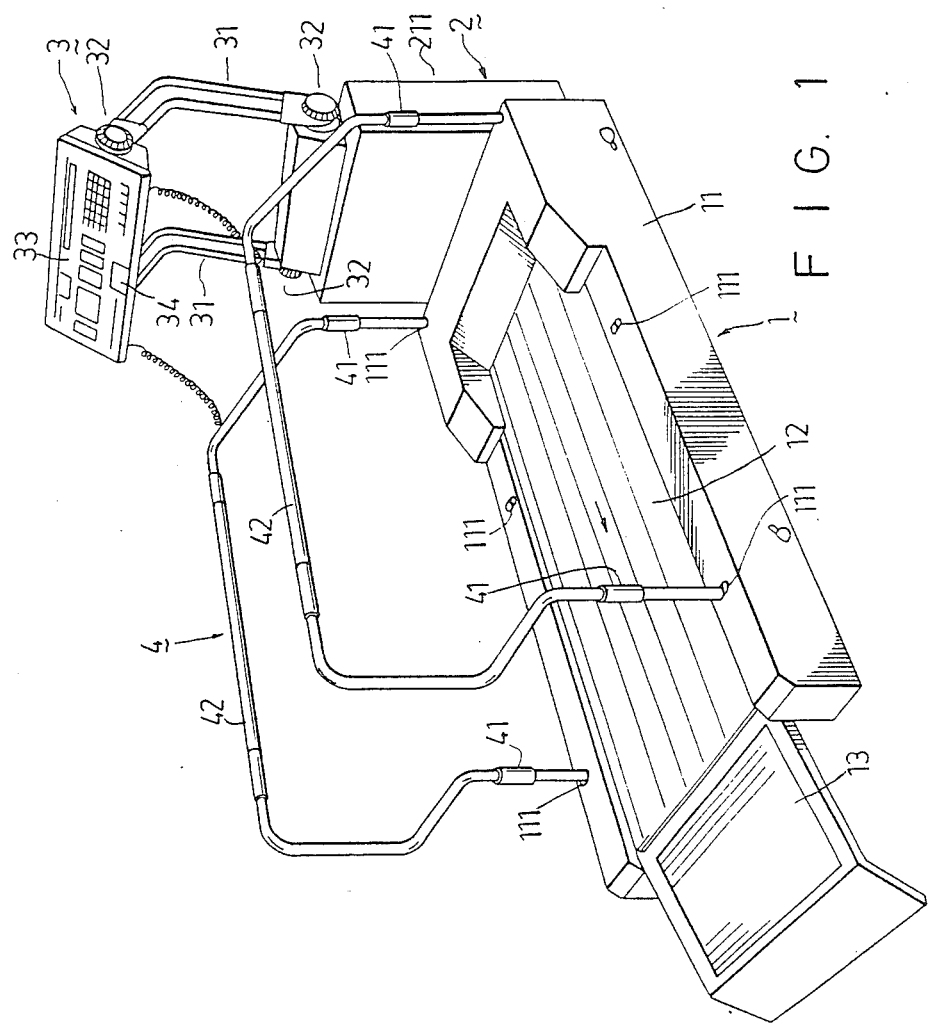
FIG. 1 is a perspective view of the treadmill according to the present invention.

Referring to FIG. 1, which shows a perspective view of a treadmill of the present invention, the treadmill consists substantially of a track means 1, a slope adjusting means 2, a controller 3 and handrails 4.

Still referring to FIG. 1 but with reference to FIGS. 2A, 2B and 2C, the track means 1 consists of an outer casing 11 with a tread belt 12 installed in the middle portion thereof. There are series of fitting holes 111 formed on the outer casing 11 for the installation of the handrails 4 and also for adjusting the distance between the two opposing handrails 4. A front stand 13 is connected to the belt 12 of the track means 1 for the user's convenience in getting on and off the tread belt.

Referring now particularly to FIGS. 2A and 2B, the track driving means 14 consists of a motor 141 connected by a rotation member 15 to a belt. The rotation member 15 is substantially in the shape of an elongated cylinder which will hold and stretch the belt 12 in cooperation with a second rotation member 16. There is a platform 17 beneath the belt 12 for supporting the weight of the user. A photo counter 18 is provided near the motor 141 for detecting the total distance the belt 12 has rotated. The distance data will be input to the controller 3.

Referring now to FIG. 2C, the slope adjusting means 2 consists of a vertical casing 211 with a reversible motor 21 installed therein. There is a gear 29 on the shaft of the motor 21 coupled to a passive gear 28 which is fixed on a horizontal axle 22. There are a pair of gears 23 at the opposite ends of the axle 22. The gears 23 are coupled to two racks 24, each of which has a bore fitted into a support 25. Two bearings 212 are sleeved on axle 22 and connected onto the vertical casing 211. Also on the casing 211 are provided a plurality of limit switches 27 along and beside the racks 24. Each limit switch 27 represents a certain predetermined slope of the track means 1.

In operation, when motor 21 starts to rotate in a direction A, the axle 22 together with the gears 23 thereon will rotate in the direction B through the coupling of gear 29 and passive gear 28. The casing 211 will then rise by pivoting about support 112 to a certain sloped condition as shown by the dotted line in FIG. 2A. When the desired slope is reached, then the limit switch 271 representing that slope is touched and pressed by the protrusion 241 on the racks 24. Then the motor 21 will stop, and the track means 1 will remain at that slope. There is further provided a photo counter 26 close to the axle 22 for detecting the slope data and inputting the data to the controller 3.

Figure 3:
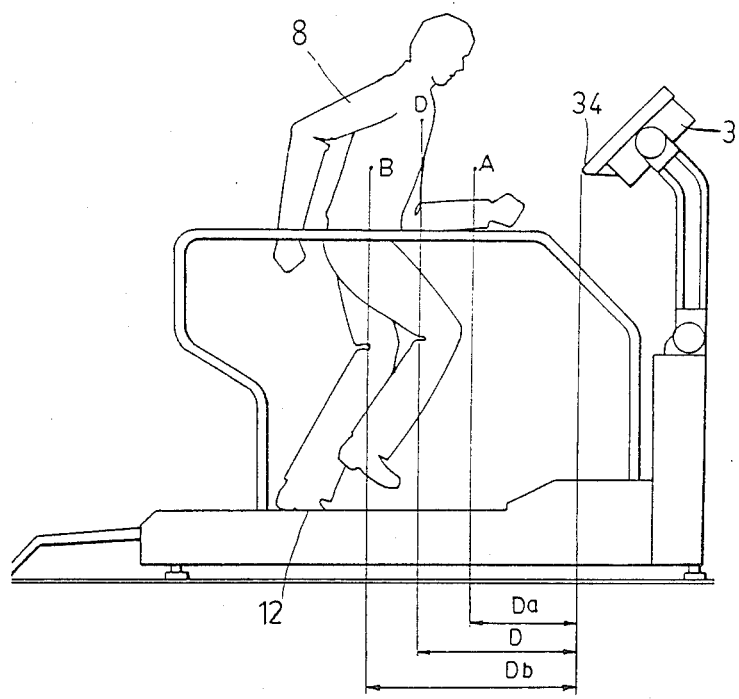
FIG. 3 is an illustrative elevation view showing the detection of the position of the user by the ultrasonic device.

Referring to FIG. 3, which is an illustrative view of the treadmill, the chest portion of the user will receive and reflect the wave transmitted by the ultrasonic device 34 on the controller 3. If the running speed of the user is faster than the speed of the belt 12, for example, if the user is at the A position $Da < D$, the controller 3 will accelerate the speed of the belt 12 each time by a certain speed unit. On the contrary, if the running speed of the user is slower than the speed of the belt 12, i.e. $Db > D$, the controller 3 will automatically slow down the belt speed.

Figure 4:
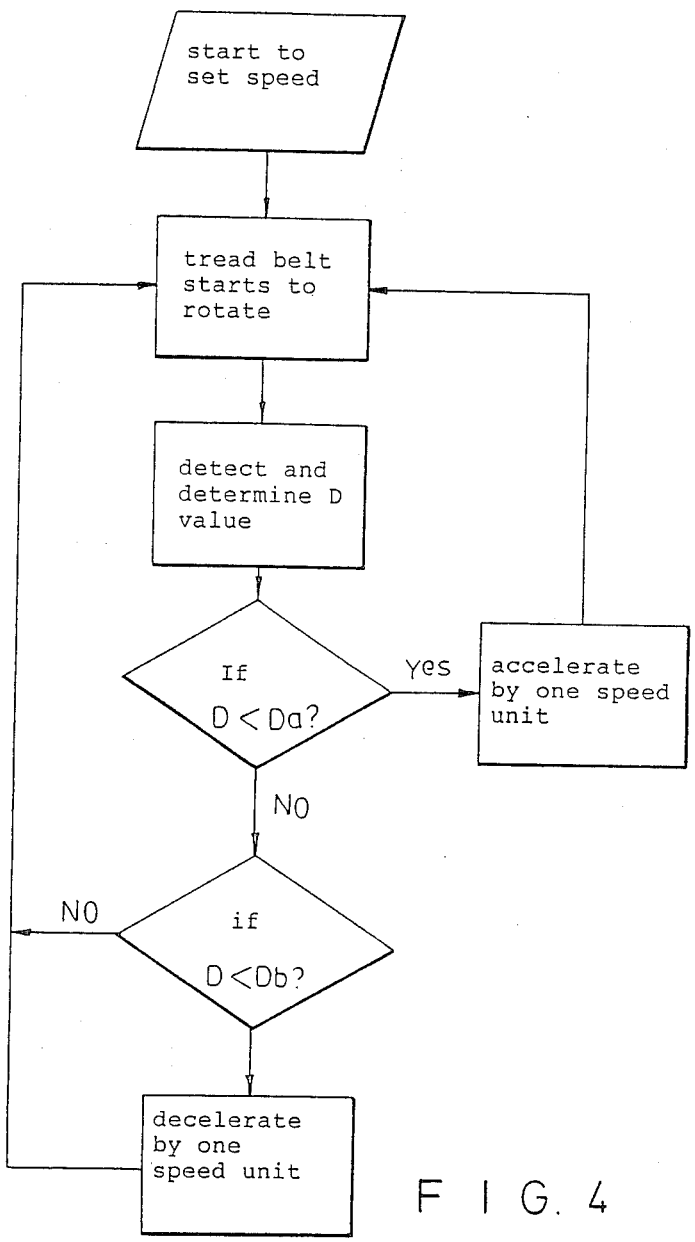
FIG. 4 is a flow chart for the speed control system program.

A microprocessor preprogrammed with software is provided within the controller 3. The various programs for different functions will be described hereinafter. Now, referring to FIG. 4, the particular flow chart is detailed for the speed controlling program. It is easily understood by the flow chart how the speed of the belt is accelerated or decelerated.

Referring now to FIG. 5 with reference to FIG. 1, on handrail 4 is formed height adjusting means 41. The handrail 4 actually consists of an inner tube 414 and an outer tube 415 clamped by a nut 411. There is a grip 413 on the outer tube 415 touching the tapered portion 412 of the nut 411. When the nut 411 is turned loose, the grip 413 on the outer tube 415 is released due to its flexibility. Thus, the inner tube 414 and outer tube 415 may be moved relative to each other to adjust the height of the handrail 4. After the desired height is reached, one can turn tight the nut 411 for a tight fit between the inner and outer tubes. Referring particularly to FIG. 1, there are safety membrane switches 42 formed on the handrail 4. The user must grip the safety switches 42 to start operation of the treadmill. This serves as a safety guard for the user, especially in therapy.

Referring to FIG. 6, which shows a perspective view of the pulse rate detector and the detector of the number of steps taken, the pulse rate detector 71 is clamped to any fingertip, preferably, the thumb, to sense the pulse, and the detector 72 is hung on the user's body for sensing the number of steps taken. Both detectors are linked together through electric wires 73 and 74 and connected to the controller 3 by an adapter 75.

Figure 7:
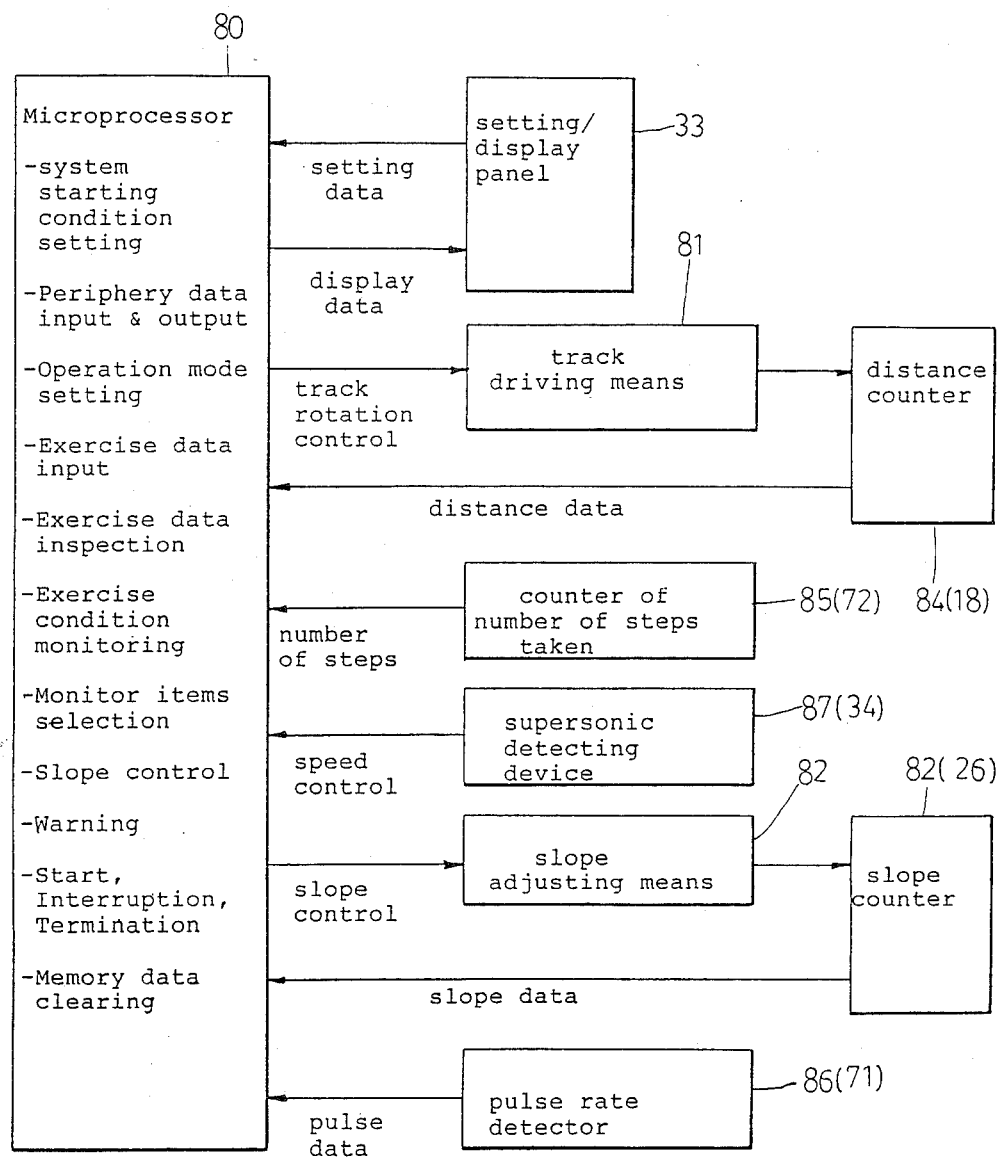
FIG. 7 is a structural diagram of the functions of the treadmill according to the present invention.

Referring to FIG. 7, which shows a structural diagram of the functions of the treadmill, the central processing unit or microprocessor 80 is connected to different control means such as setting/display panel 33 for setting and displaying data. By track driving means 81 and slope adjusting means 82, the functions of track belt rotation control and slope control will be executed. The data sensed by slope counter 82 (26), distance counter 84 (18) and ultrasonic detecting device 87 (34) serves as reference for controlling the slope and the speed. Collecting the data sensed by the distance counter 84 (18) and the counter of the number of steps taken 85 (72), the microprocessor 80 can store or display data concerning distance, the number of steps taken and the pace. With the pulse rate detector 86 (71), the pulse rate data also may be collected and processed by the microprocessor 80. The functions that microprocessor 80 can perform are briefly listed in FIG. 7, but a detailed list of possible functions can be found in Table 1. Those functions operable before starting the track rotation operation are listed in Table 2. Functions operable during track rotation are listed in Table 3. Functions operable during interruption of the rotation are listed in Table 4, and possible functions of the treadmill are listed in Table 5.

Figure 8:
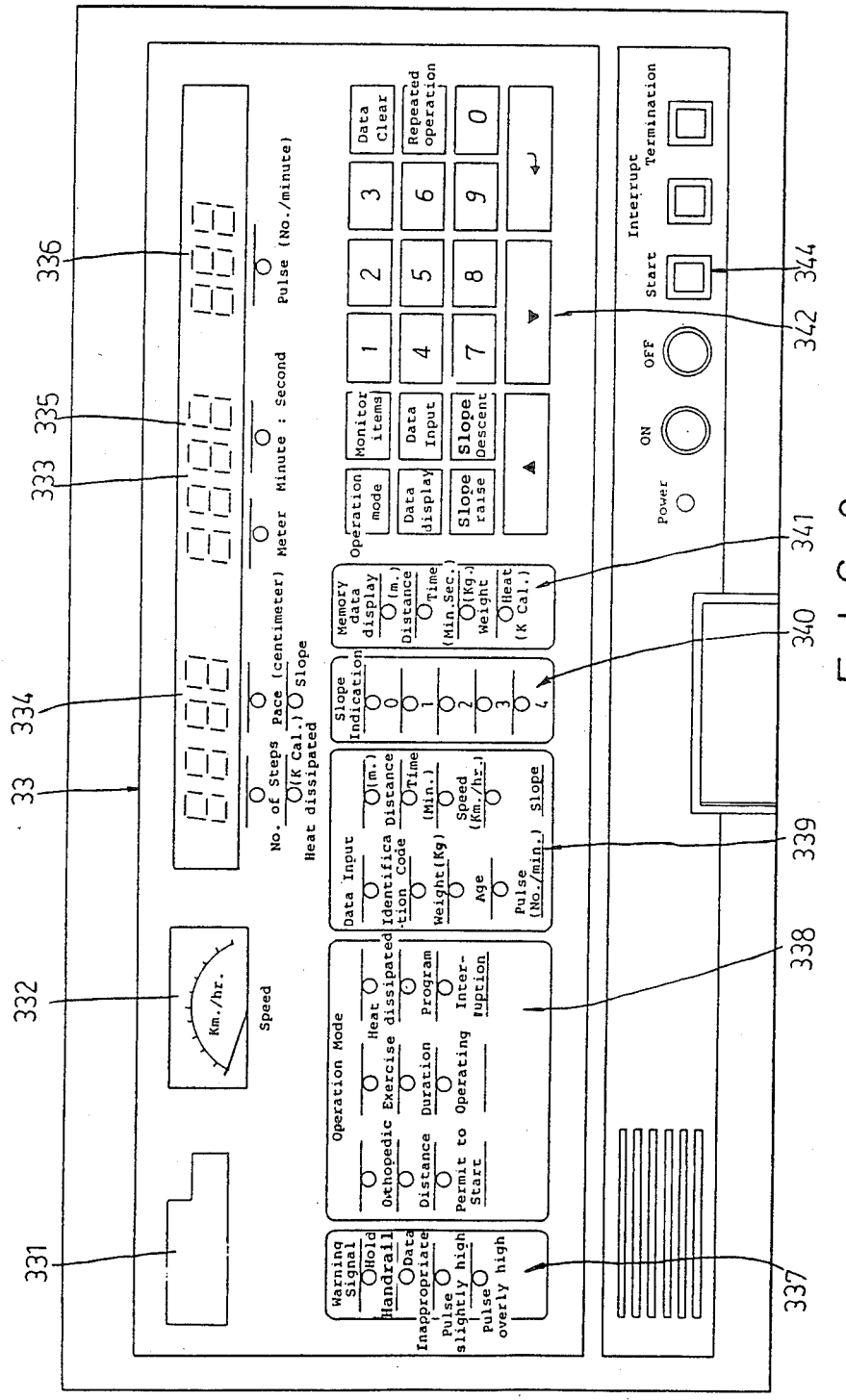
FIG. 8 is an elevation diagram of a front panel of the controller of the treadmill according to the present invention.
Figures 7, 15:
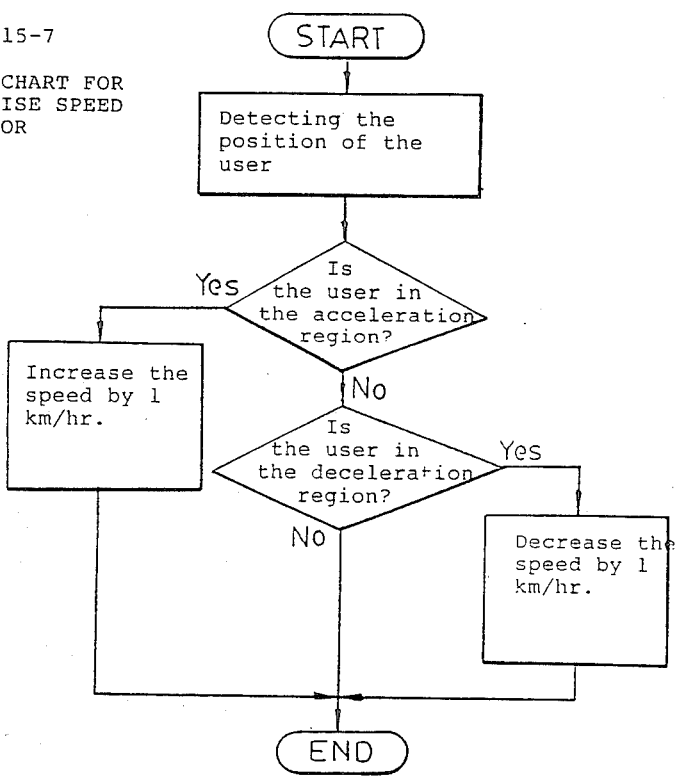
Figures 8, 15:
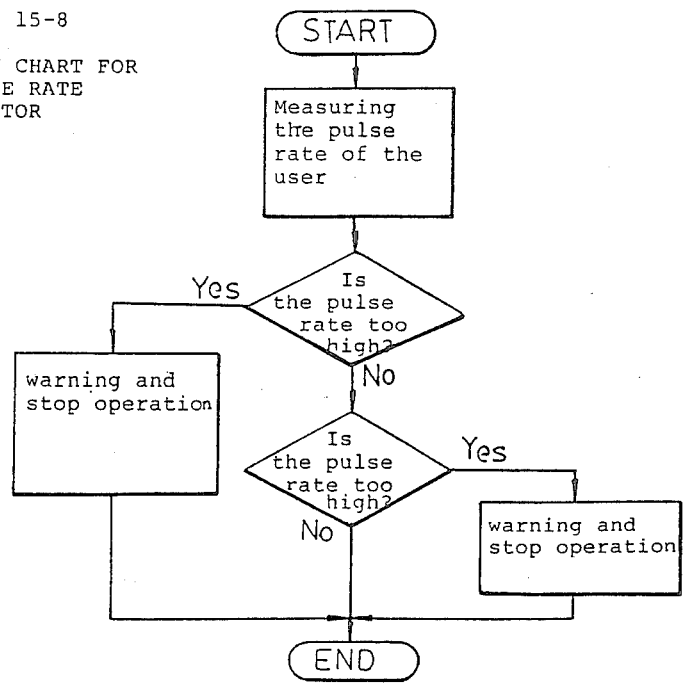
Figures 16, 17:
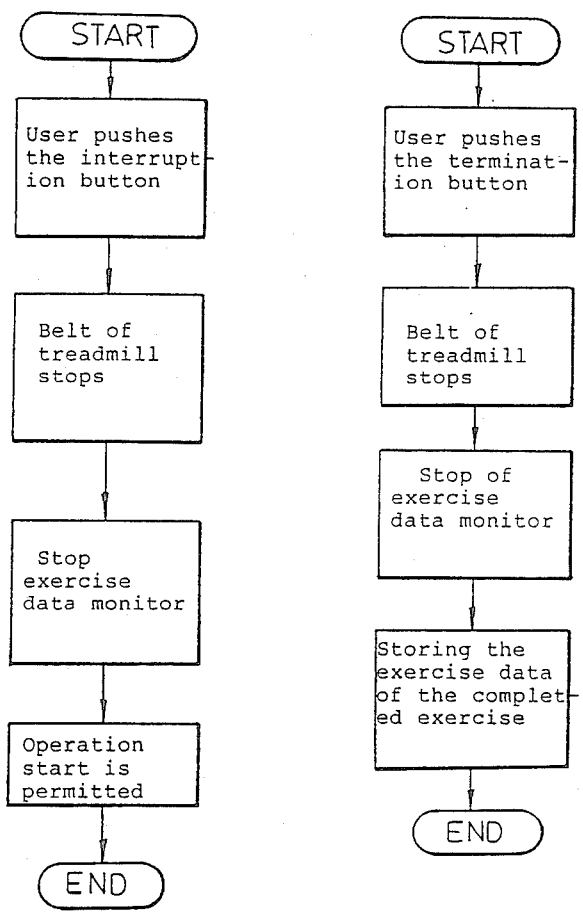
FIG. 16 is a flow chart for the program of interruption of the operation.
FIG. 17 is a flow chart for the program of termination of the operation of the treadmill.

Referring to FIG. 8, which shows the diagram of the front panel of the controller 3 of the treadmill, there is a name plate 331, a belt speed meter 332 and display panel 333 on the upper portion. The display panel 333 further consists of a display 334 for displaying the number of steps, pace, heat dissipated and slope, a display 335 for distance and time, and a display 336 for pulse rate. The middle portion of the panel 33 has a set of input and control keys 342 on the right and lights together with specifications on the left. There is a warning signal light group 337, operation status lights group 338, data input lights group 339, slope indication lights group 340 and memory data display lights group 341 shown on the controller panel 33. There are other buttons for power, ON, OFF, control button 344 for START, and INTERRUPTION, and TERMINATION buttons shown on the bottom portion of the panel 33.

When the user wants to exercise on the treadmill, he must first touch "the operation mode" button and choose the operation mode displayed desired from the operation status lights group 338. Then, he must push the input key 342 for inputting all the necessary exercise data such as an identification code, weight, age, distance to be covered, period of exercise, speed, etc., indicated in the data input lights group 339. After data are input, the user then pushes the START button, causing the treadmill to start operation in accordance with the prestored reference data, and as the treadmill operates the microprocessor 80 will continue to perform all the functions possible, such as adjusting speed/slope, generating warning signals, displaying exercise data, etc.

There are programs for different functions stored in the microprocessor 80 which are listed in Table 5, and the flow charts for these programs are shown respectively in FIG. 9 through FIG. 20. The functions and their associated programs/flow charts are quite self-explanatory and thus will not be detailed further. However, it is to be understood and noted that further possible functions can still be very easily developed and added to the treadmill of the present invention.

The treadmill of the present invention has been described hereinabove by way of a preferred embodiment; it is to be noted that changes, improvements, and modifications can still be made without departing from the scope of the present invention.

TABLE 1

List of possible functions of the treadmill

1. Selection of exercise or therapeutic function
2. Selection among functions of distance covered, duration of exercise or program mode
3. Selection among functions of number of steps taken, pace, heat dissipated or slope adjustment
4. Setting operation data function
5. Repeating operation function
6. Displaying memory data function
7. Clearing memory of data function
8. Slopes adjustment
9. Starting operation function
10. Interrupting operation function
11. Terminating operation function
12. Searching forward for data in memory
13. Searching backward for data in memory
14. Monitoring exercise data function

TABLE 2

List of functions performable before starting rotation operation

1. Selection of exercise or therapeutic function
2. Selection among functions of distance covered, duration of exercise or program mode
3. Selection among functions of number of steps taken, pace, heat dissipated or slope adjustment
4. Setting operation data function
5. Repeating operation function
6. Displaying memory data function
7. Clearing memory of data function
8. Slopes adjustment
9. Starting operation function
10. Searching forward for data in memory
11. Searching backward for data in memory

TABLE 3

List of functions performable during rotation operation

1. Interrupting operation function
2. Terminating operation function
3. Monitoring exercise data function

TABLE 4

List of functions performable during interruption

1. Selection among functions of number of steps taken, pace, heat dissipated or slope adjustment
2. Displaying memory data function
3. Searching forward for data in memory
4. Search backward for data in memory
5. Slopes adjustment
6. Starting operation function TABLE 4-continued List of functions performable during interruption 7. Terminating operation function

TABLE 5

Software Modes of Treadmill

1. System starting condition setting mode
2. Periphery data inputting mode
3. Operation modes selecting mode
4. Monitor items selecting mode
5. Exercise data setting mode
6. Permission for starting mode
7. Exercise repeating mode
8. Memory data displaying mode
9. Memory data clearing mode
10. Slope adjusting mode
11. Data backward-searching mode
12. Data forward-searching mode
13. Operation starting mode
14. Operation interruption mode
15. Operation termination mode
16. Exercise data monitoring mode
17. Periphery data outputting mode
18. Exercise duration interrupting mode

What is claimed is:

1. A treadmill having track means for rotating a rotatable belt for a user to stand upon, driving means with a power apparatus connected to said track means for driving said rotatable belt to rotate within a range of speeds ranging from zero to a predetermined maximum and slope adjusting means associated with said track means for inclining said track means, comprising:

a microprocessor controller having stored therein software programs corresponding to a function and a control arrangement for the function, said controller further including data input means for inputting reference control data, data storage means for storing data, and display means for displaying data; and exercise data detecting means for sensing exercise data and inputting the same to said controller, said exercise data detecting means including means for detecting a user's position and means for inputting data representative of the user's position relative to said controller for adaptively changing the speed of the rotatable belt to keep the user at a certain position on said track means, wherein said slope adjusting means is controlled responsive to said exercise data by said controller to change the slope of said track means, and said driving means is controlled by said controller responsive to said exercise data to vary the speed of rotation of said rotatable belt.

2. A treadmill according to claim 1 wherein said means for detecting the user's position is an ultrasonic transmitter and receiver.

3. A treadmill according to claim 1 wherein said function/control arrangement within said controller further includes means for setting operation modes including a distance mode, a duration of exercise mode, a heat dissipation mode, a program mode, and a repeat operation mode.

4. A treadmill according claim 3 wherein said function/control arrangement controls the distance rotated by said rotatable belt of the track means when the exercise mode is set at the distance mode.

5. A treadmill according to claim 3 wherein said function/control arrangement controls a period of operation of the belt of the track means when the exercise mode is set at the duration mode.

6. A treadmill according to claim 3 wherein said function/control arrangement controls the track means to operate in accordance with a predetermined program when the exercise mode is set at the program mode.

7. A treadmill according to claim 1 wherein said function/control arrangement further includes means for monitoring exercise conditions including distance, time, number of steps, heat dissipation, pulse rate, speed of belt rotation and slope of track means.

8. A treadmill according to claim 1 wherein said function/control arrangement within said controller further includes warning means for generating an output warning signal when the data concerning the pulse rate of the user is abnormal, said warning signal also being generated during a change of speed and slope of the track means, wherein when the pulse rate is too high, the track driving means ceases operation.

9. A treadmill having track means for rotating a rotatable belt for a user to stand upon, driving means with a power apparatus connected to said track means for driving said rotatable belt to rotate within a range of speeds ranging from zero to a predetermined maximum and slope adjusting means associated with said track means for inclining said track means, comprising:

a microprocessor controller having stored therein software programs corresponding to a function and a control arrangement for the function, said controller further including data input means for inputting reference control data, data storage means for storing data, and display means for displaying data;

exercise data detecting means for sensing exercise data and inputting the same to said controller, wherein said slope adjusting means is controlled responsive to said exercise data by said controller to change the slope of said track means, and said driving means is controlled by said controller responsive to said exercise data to vary the speed of rotation of said rotatable belt and handrails installed at each side of said track means, and a plurality of safety switches formed on said handrails, said safety switches turning ON only when the user holds the handrails such that the treadmill will terminate operation when the user's hand leaves the handrails.

* * * * *